United States Patent
Hawkins

[19]

[11] Patent Number: 6,095,993
[45] Date of Patent: Aug. 1, 2000

[54] ADJUSTMENT ARM SLING

[76] Inventor: Kevin Hawkins, 534 S. Park Ave., Fremont, Ohio 43420

[21] Appl. No.: 09/133,266

[22] Filed: Aug. 13, 1998

[51] Int. Cl.$^7$ ....................................................... A61F 5/00
[52] U.S. Cl. .................................................................. 602/4
[58] Field of Search .............................. 602/4, 5, 19, 20, 602/60–62; 128/877, 878; 224/637, 625, 664

[56] References Cited

U.S. PATENT DOCUMENTS

| | | |
|---|---|---|
| 2,111,963 | 3/1938 | Coombs . |
| 3,103,216 | 9/1963 | Scott . |
| 3,554,194 | 1/1971 | Johnson ......................................... 602/4 |
| 4,497,316 | 2/1985 | Lilla . |
| 4,598,702 | 7/1986 | Lilla . |
| 4,751,923 | 6/1988 | Merino ................................. 128/878 X |
| 4,759,353 | 7/1988 | Melendez et al. . |
| 4,991,758 | 2/1991 | Eaneff ........................................ 224/625 |
| 5,001,791 | 3/1991 | Toso ....................................... 602/19 X |
| 5,141,488 | 8/1992 | Schrader ............................. 128/878 X |
| 5,413,552 | 5/1995 | Iwuala . |
| 5,830,165 | 11/1998 | Rowe et al. .................................. 602/4 |

*Primary Examiner*—Richard J. Apley
*Assistant Examiner*—Denise Pothier
*Attorney, Agent, or Firm*—Harpman & Harpman

[57] ABSTRACT

A universal adjustable arm sling consisting of a sling pad with an adjustable attachment strap. An adjustable support strap extends from the attachment strap over the shoulder of the user and diagonally across the back and around the opposite side of the user's body. The adjustable support strap is engageable with the adjustable attachment strap of the sling for support strap length adjustment for the sling pad.

1 Claim, 4 Drawing Sheets

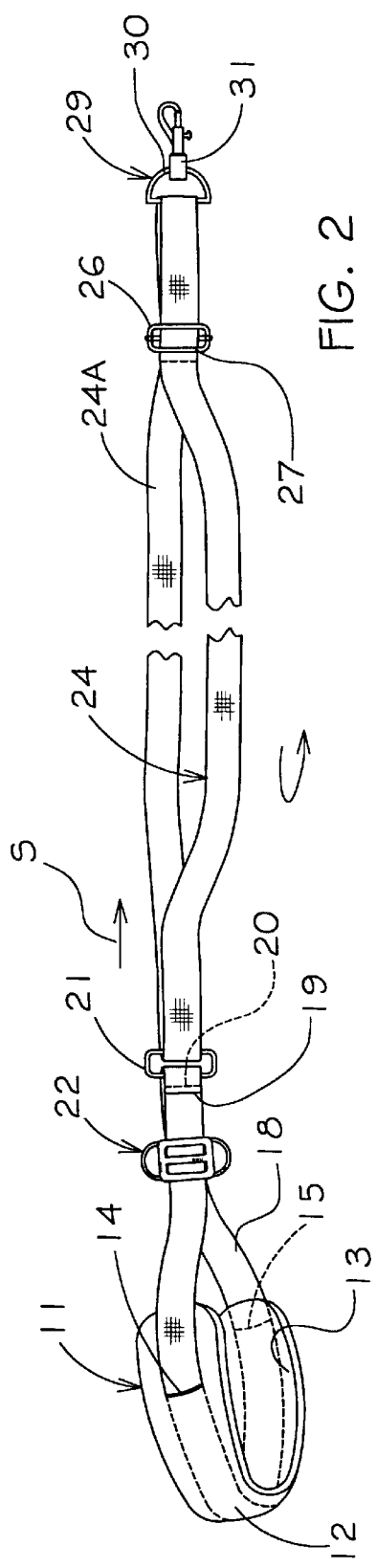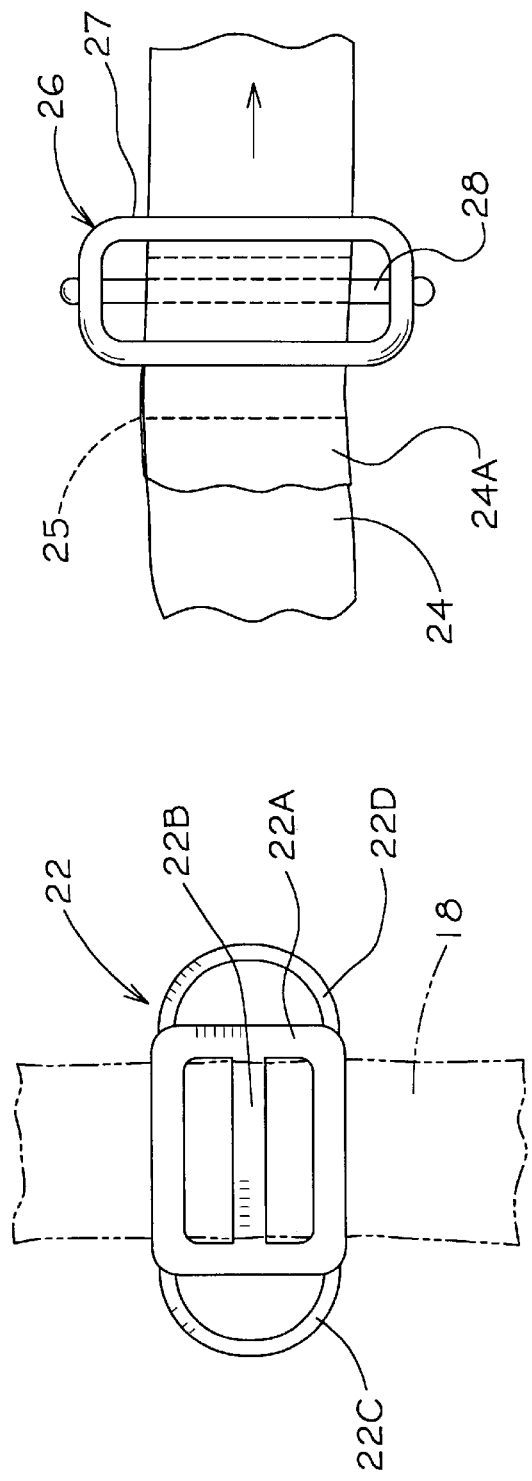

ADJUSTMENT ARM SLING

BACKGROUND OF THE INVENTION

1. Technical Field

This invention relates to sling devices that are used to support and immobilize a body member, specifically the forearm in a prescribed position across the body.

2. Description of Prior Art

Prior art devices of this type have shown a variety of different arm sling configurations with arm and sling portions and engagement strap, see for example U.S. Pat. Nos. 2,111,963, 3,103,216, 4,497,316, 4,598,702, 4,759,353 and 5,413,552.

In U.S. Pat. No. 2,111,963 an arm sling is disclosed having an arm sling with a pair of straps extending therefrom over respective shoulders of the users with a single strap on the back engageable to the waist belt.

U.S. Pat. No. 3,103,216 is directed to a arm sling having a pair of spaced shoulder engagement straps extending from oppositely disposed sides of the sling with an interconnection strap therebetween.

U.S. Pat. Nos. 4,497,316 and 4,598,702 both disclose a cantilevered suspension sling having two-part arm support members with a yoke strap and a shoulder strap extending therefrom. The shoulder strap extends around the wearer's body and is adjustably secured to the portion of the arm support that holds the elbow of the user.

U.S. Pat. No. 4,759,353 is for a universal forearm sling having a shoulder strap extending fore and aft therefrom. A waist strap extends around the body of the user and attaches at two independent points to the sling.

U.S. Pat. No. 5,413,552 illustrates an arm sling with hummeral stabilizer and includes an arm pouch with an adjustable shoulder strap extending therefrom and a second shoulder strap engageable on a torso belt.

SUMMARY OF THE INVENTION

A fully adjustable forearm sling for supporting and immobilizing a patient's arm for therapeutic reasons. The adjustable sling has a double adjustment support strap that is adjustably secured to an arm sling by an attachment strap that extends fully around the arm sling. The opposite end of the support strap extends over the patient's shoulder adjacent the supported arm and across the back of the patient and around a portion of the torso opposite the sling being selectively secured to a length adjustment and loop buckle on the attachment strap extending from the sling.

DESCRIPTION OF THE DRAWINGS

FIG. 2 is a perspective view of the instant invention;

FIG. 3 is a front elevational view of an adjustment fixation buckle;

FIG. 4 is a front elevational view of an adjustment strap of the invention;

DESCRIPTION OF THE PREFERRED EMBODIMENT

Figure 5:
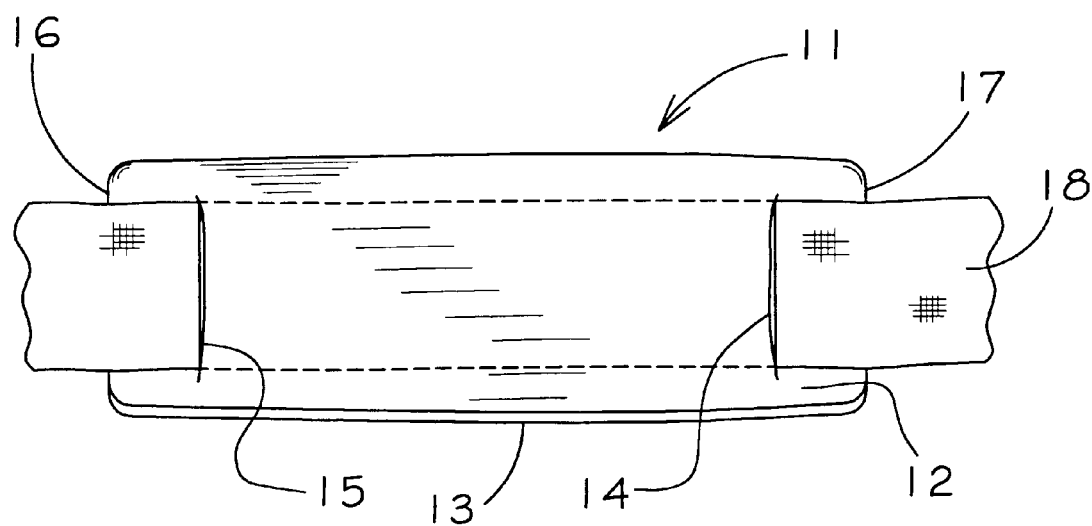
FIG. 5 is a partial elevational view of the arm engagement sling portion of the invention.

Referring now to FIGS. 1, 2, 5 and 6 of the drawings, an arm sling 10 can be seen having a generally rectangular sling pad 11 with an outer surface 12 and a padded inner surface 13. The outer and inner surfaces 12 and 13 are registerably secured together around their respective perimeter edges. Engagement openings 14 and 15 are formed transversely within the outer surface 13 inwardly of the respective oppositely disposed ends 16 and 17 of the engagement pad 11 as best seen in FIGS. 2 and 5 of the drawings. An attachment strap 18 extends through said openings 14 and 15 between the inner and outer surfaces 12 and 13 respectively with the straps free ends 19 and 20 secured to one another about an extension buckle 21. An adjustment and attachment buckle fitting 22 is threadably positioned on the attachment strap 18 adjacent the extension buckle 21 to provide strap adjustment to correspond to the placement of the patient's forearm 23 through the sling formed by the strap 18 and sling pad 11. An adjustable support strap 24 extends through the extension buckle 21 with one end of the strap at 25 shown in dotted lines being secured to a length adjustment buckle 26 that has a rectangular open wire frame 27 defining a strap opening and a movable anchor bar 28 extending therebetween as will be well understood by those skilled in the art.

The support strap 24 returns back upon itself from the extension buckle 21 and through the adjustment buckle 26 as indicated by 24A and the arrow S shown in FIG. 4 of the drawings.

Figure 7:
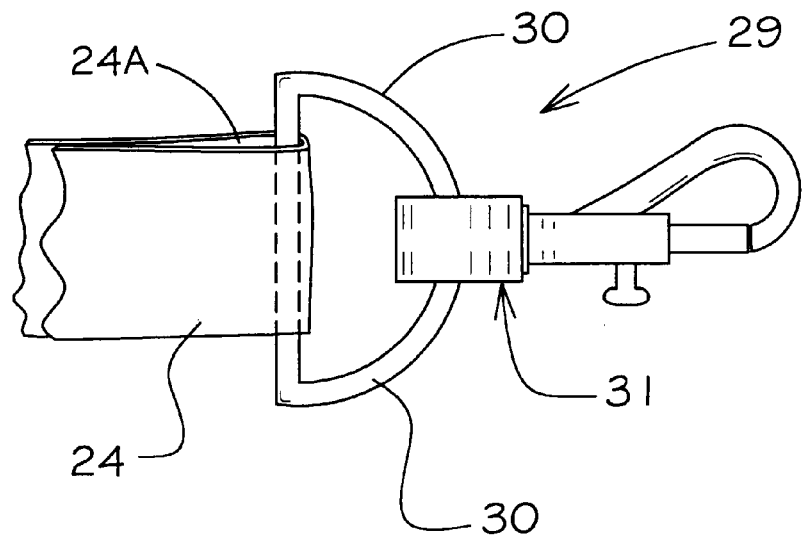
FIG. 7 is a front elevational view of the adjustment attachment buckle.

A swivel buckle fitting 29, best seen in FIG. 2 of the drawings, has a strap engagement loop fitting 30 with a swivel snap attachment fitting 31 as best seen in FIG. 7 of the drawings, as will be understood by those skilled in the art, extending therefrom which allows for selective removal attachment to the hereinbefore described buckle fitting 22.

The attachment and support straps 18, 24 and 24A respectively are preferably made of a reinforced woven nylon material, but can be of any suitable material acceptable within the art.

Figure 1:
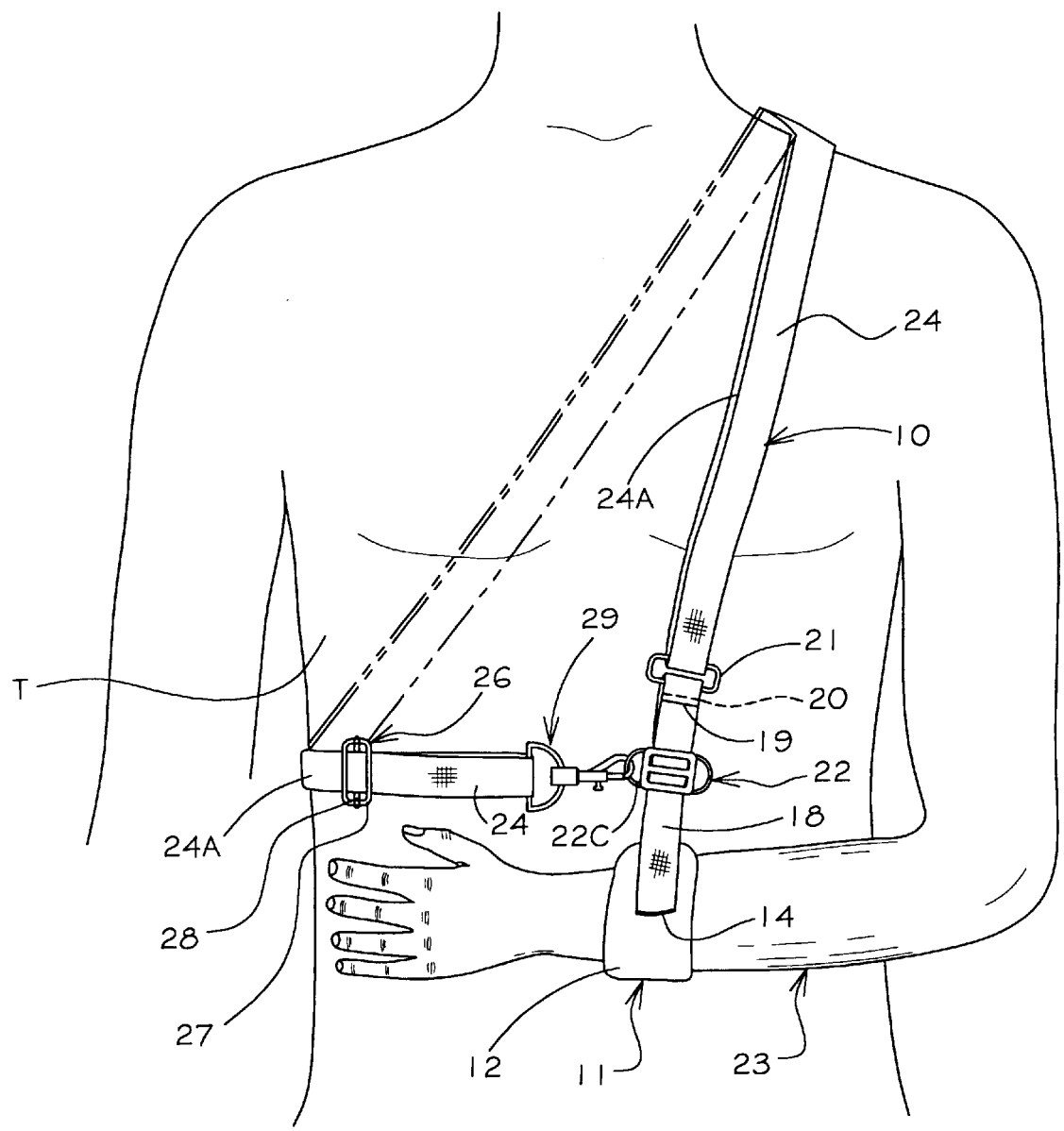
FIG. 1 is a front elevational view of the instant invention on a patient.
Figure 6:
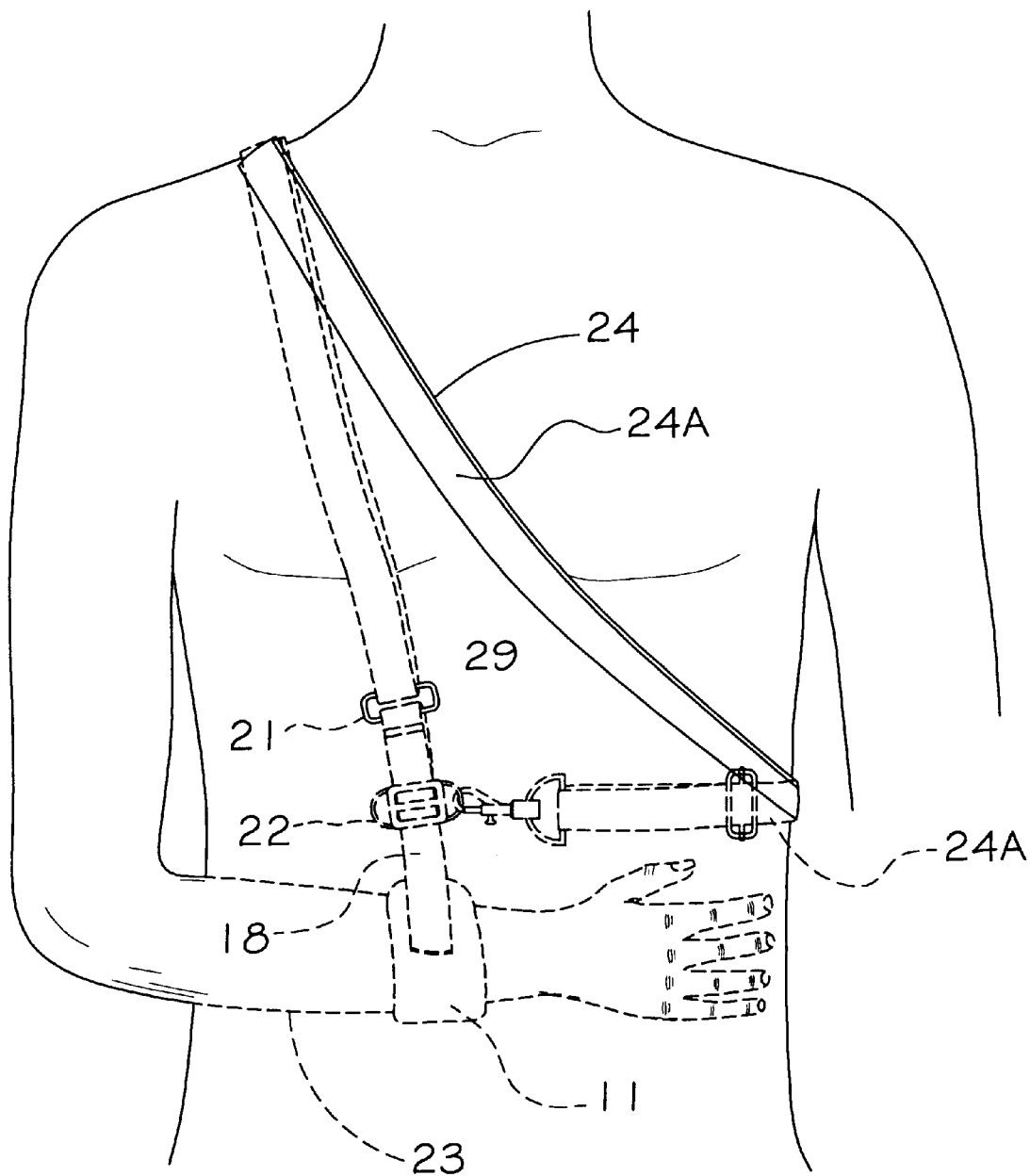
FIG. 6 is a back elevational view of the instant invention on a patient with portions shown in dotted lines.

In use, as best seen in FIGS. 1 and 6 of the drawings, the arm sling of the invention provides for universal length and arm use requirements. The patient's forearm 23 is inserted through the engagement loop formed by the pad 11. The attachment strap 18 extending about and through the pad 11 is then adjusted, if necessary, by movement of the adjustable attachment buckle fitting 22, best seen in FIG. 3 of the drawings. The buckle fitting 22 has a rectangular buckle brace 22A with an inturned fixed cross element 22B, and oppositely disposed snap engagement loops 22C and 22D. The adjustable support strap 24 extends from the attachment strap 18 over a shoulder of the patient's forearm 23 and then diagonally across the patient's back as shown in dotted lines in FIG. 1 of the drawings and solid lines in FIG. 6 of the drawings.

The support strap 24 and 24A then extends around the side portion of the patient's torso T in spaced parallel relation to the patient's forearm 23.

The support strap 24 can be adjusted in length by the adjustment buckle 26 to accommodate a wide variety of body shapes and sizes utilizing the "returned" strap material at 24A hereinbefore described.

The attachment snap buckle 29 is selectively secured to the engagement loop 22C of the adjustable attachment buckle fitting 22 completing the arm sling 10 of the invention.

It will be evident from the above description that the arm sling 10 can be used on either arm of the patient by simply reversing its orientation. The arm sling of the invention will significantly reduce neck and shoulder strain on the patient by providing dual support to the effective limb by balancing the natural vertical forces of gravity imparted to the support straps by the patient's arm 23 across the patient's back and torso T.

It will thus be seen that a new and novel arm sling has been illustrated and described and it will be apparent to those skilled in the art that various changes and modifications may be made thereto without departing from the spirit of the invention.

Therefore I claim:

1. An improved sling for a patient's arm comprising: an arm sling pad, an attachment strap extending about said arm sling pad defining an arm engagement loop, a support strap extending from said attachment strap adapted to extend over the shoulder of the patient's arm positioned within said arm sling pad, said support strap having an adjustment means thereon for overall length adjustment, means for selectively securing said support strap to said attachment strap at a point midway between said sling pad and said support strap attachment point, wherein said means for selectively securing said support strap to said attachment strap comprises an adjustment and attachment buckle fitting on said attachment strap, and registering swivel snap buckle fitting on said support strap, said adjustment and attachment buckle comprising a buckle fitting and a pair of oppositely disposed snap engagement loops extending therefrom for registration with said swivel snap buckle.

\* \* \* \* \*